US006846652B2

(12) United States Patent
Jacobs et al.

(10) Patent No.: US 6,846,652 B2
(45) Date of Patent: Jan. 25, 2005

(54) VIRAL VECTORS HAVING ENHANCED EFFECTIVENESS WITH REDUCED VIRULENCE

(75) Inventors: Bertram Jacobs, Tempe, AZ (US); Teresa A. Brandt, Tempe, AZ (US)

(73) Assignee: Arizona Board of Regents, Tempe, AZ (US)

( * ) Notice: Subject to any disclaimer, the term of this patent is extended or adjusted under 35 U.S.C. 154(b) by 246 days.

(21) Appl. No.: 09/887,295

(22) Filed: Jun. 22, 2001

(65) Prior Publication Data

US 2002/0110565 A1 Aug. 15, 2002

Related U.S. Application Data

(63) Continuation-in-part of application No. PCT/US00/10948, filed on Dec. 7, 2000.
(60) Provisional application No. 60/136,277, filed on May 27, 1999.

(51) Int. Cl.[7] .................. C12N 15/863; C12N 15/63
(52) U.S. Cl. ............... 435/69.3; 435/69.1; 435/320.1; 435/455; 435/456; 424/184.1; 424/204.1; 424/232.1; 424/93.1; 424/93.2; 424/93.6
(58) Field of Search ........................... 435/69.1, 91.41, 435/320.1, 69.3, 455, 456; 536/23.72, 23.1; 424/184.1, 204.1, 232.1, 93.1, 93.2, 93.6

(56) References Cited

U.S. PATENT DOCUMENTS 6,004,777 A   12/1999  Tartaglia et al. ........... 435/69.1

OTHER PUBLICATIONS

Beattie et al., Virus Genes 12:1, 89–94, 1996.*
U.S. Appl. No. 09/837,998 to Jacobs et al., filed Apr. 19, 2001.
U.S. Appl. No. 09/837,997 to Jacobs et al., filed Apr. 19, 2001.
Beattie et al., "Reversal of the Interferon–Sensitive Phenotype of a Vaccinia Virus Lacking E3L by Expression of the Reovirus S4 Gene", Journal of Virology, vol. 69, No. 1, Jan. 1995, pp. 499–505.
Brandt et al., "Both Carboxy– and Amino–Terminal Domains of the Vaccinia Virus Interferon Resistance Gene, E3L, Are Required for Pathogenesis in a Mouse Model", Journal of Virology, vol. 75, No. 1, Jan. 2001, pp. 850–856.
Chang et al., "Indentification of a Conserved Motif That Is Necessary for Binding of the Vaccinia Virus E3L Gene Products to Double–Stranded RNA", Virology, vol. 194, 1993, pp. 537–547.
Kibler et al., "Double–Stranded RNA Is a Trigger for Apoptosis in Vaccinia Virus–Infected Cells", Journal of Virology, vol. 71., No. 3, Mar. 1997, pp. 1992–2003.
Shors et al., "Complementation of Vaccinia Virus Deleted of the E3L Gene by Mutants of E3L", Virology, vol. 239, 1997, pp. 269–276.

* cited by examiner

*Primary Examiner*—Laurie Scheiner
(74) *Attorney, Agent, or Firm*—Baker Botts L.L.P.

(57) ABSTRACT

The present invention provides methods of use of recombinant vaccinia virus from which the region encoding the N-terminal 83 or 54 amino acids of the E3L gene product has been deleted, or amino acids at positions 44 and 66 have been mutated. Compositions comprising the recombinant vaccinia virus are also provided.

5 Claims, 3 Drawing Sheets

VIRAL VECTORS HAVING ENHANCED EFFECTIVENESS WITH REDUCED VIRULENCE

CROSS REFERENCE TO RELATED APPLICATION

This application is a continuation-in-part of PCT/US00/10948 which application was published by the International Bureau in English on Dec. 7, 2000 and which claims priority of U.S. application Ser. No. 60/136,277 filed May 27, 1999. The disclosures of PCT/US00/10948 and Ser. 60/136,277 are incorporated herein by reference in their entireties.

STATEMENT REGARDING FEDERALLY FUNDED RESEARCH

Financial assistance for this project was provided by the U.S. Government through the National Institutes of Health under grant number CA-4865409 and the United States Government may own certain rights in this invention.

BACKGROUND OF THE INVENTION

Vaccinia virus is a member of the poxvirus family of DNA viruses. Poxviruses including vaccinia virus are extensively used as expression vectors since the recombinant viruses are relatively easy to isolate, have a wide host range, and can accommodate large amounts of DNA.

The vaccinia virus genome contains nonessential regions into which exogenous DNA can be incorporated. Exogenous DNA can be inserted into the vaccinia virus genome by well-known methods of homologous recombination. The resulting recombinant vaccinia viruses are useful as vaccines and anticancer agents.

The use of vaccinia virus recombinants as expression vectors and particularly as vaccines and anticancer agents raises safety considerations associated with introducing live recombinant viruses into the environment. Virulence of vaccinia virus recombinants in a variety of host systems has been attenuated by the deletion or inactivation of certain vaccinia virus genes that are nonessential for virus growth. However, there remains a need in the art for the development of vectors that have reduced pathogenicity while maintaining desirable properties of wild-type virus, such as host range, and active protein synthesis of a desired gene product.

SUMMARY OF THE INVENTION

The present invention provides methods of use of a recombinant vaccinia virus in which the region encoding an N-terminal portion of the E3L gene product has been mutated. In a preferred embodiment, the region encoding the N-terminal 54 or 83 amino acids of the E3L gene product has been deleted, or the amino acids at positions 44 and 66 have been mutated. The present invention further provides an expression vector comprising the recombinant vaccinia virus of the invention and exogenous DNA.

The present invention also provides a composition comprising the expression vector of the invention and a carrier and a method of making a recombinant gene product.

DETAILED DESCRIPTION OF THE INVENTION

Figure 1:
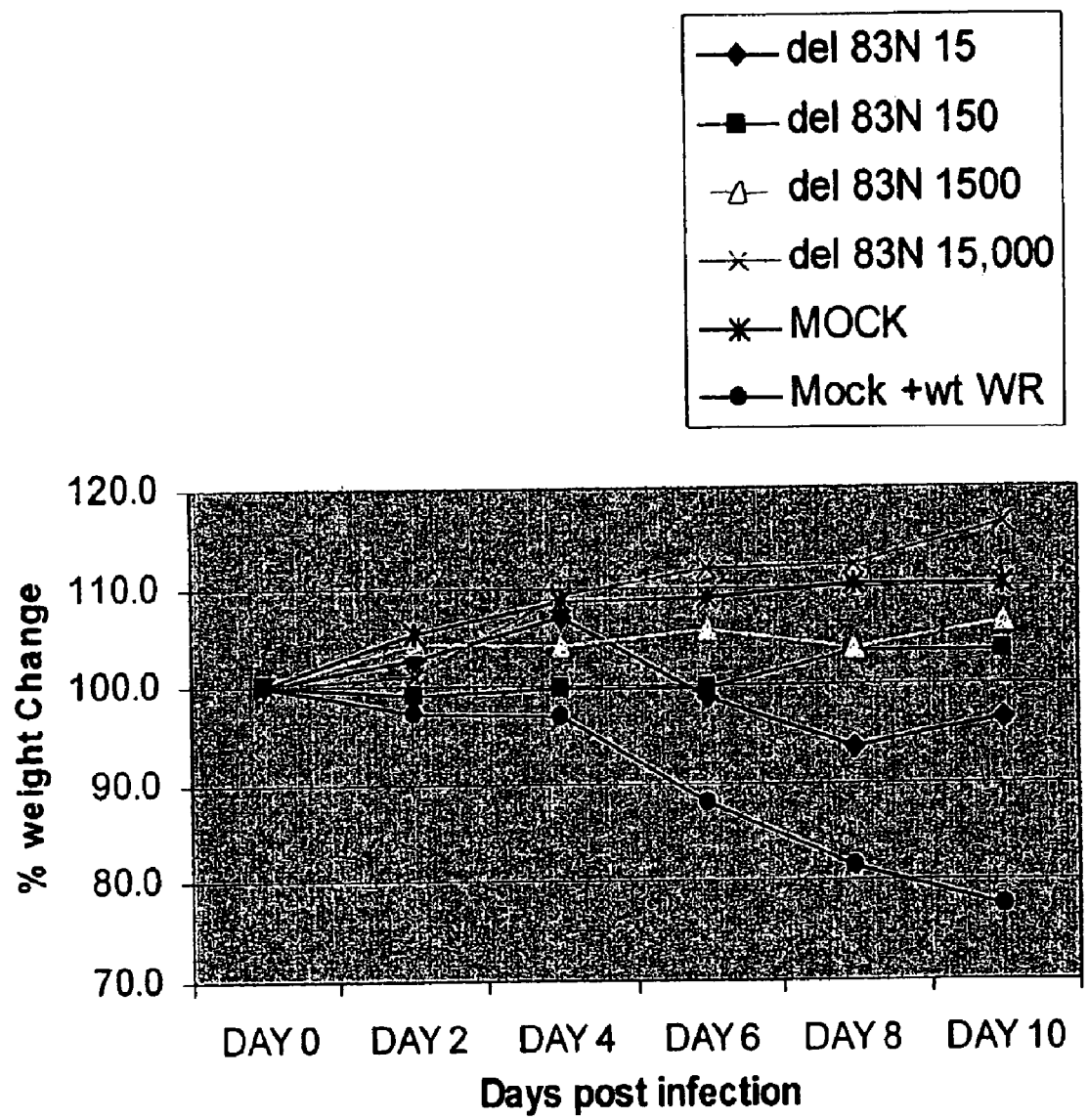
FIG. 1 is a graph showing percent weight change in mice infected with vaccina virus following immunization with WR Δ83N.

The vaccinia virus E3L gene codes for double-stranded RNA binding proteins, and has been shown to be necessary for the vaccinia virus interferon-resistant phenotype. The E3L gene product of the vaccinia virus is a 190 amino acid polypeptide. Amino acids 118 to 190 have been implicated in dsRNA binding, as disclosed by Kibler et al. (1997) *J. Virol.* 71: 1992, incorporated herein by reference.

The present invention provides a recombinant vaccinia virus in which the region of the viral genome encoding an N-terminal portion of the E3L gene product has been mutated. An N-terminal portion of the E3L gene product is defined herein as including at least amino acids 1 through 37 of the E3L gene product. Amino acid numbering as used herein is adopted from Goebel et al. (1990) *Virology* 179: 247–66, 577–63, the disclosure of which is incorporated herein by reference. An N-terminal portion of the E3L gene product as defined herein may encompass the region from the N-terminus (amino acid 1) up to and including amino acid 117. Accordingly, a mutation is present in the region encoding at least 37, and as many as 117, N-terminal amino acids of the E3L gene product in the recombinant vaccinia virus of the present invention.

The term mutation, as used herein, includes deletions, substitutions and point mutations.

In a preferred embodiment, the region of the viral genome encoding the N-terminal 83 amino acids of the E3L gene product has been deleted. In this preferred embodiment, the recombinant vaccinia virus of the present invention contains a nucleic acid fragment encoding amino acids 84–190 of the E3L gene product instead of the gene encoding amino acids 1–190 of the E3L gene product at the E3L locus of the WR strain of vaccinia virus and is designated WR Δ83N.

In another preferred embodiment, the region of the viral genome encoding the N-terminal 54 amino acids of the E3L gene product has been deleted. In this preferred embodiment, the recombinant vaccinia virus of the present invention contains a nucleic acid fragment encoding amino acids 55–190 of the E3L gene product instead of the gene encoding amino acids 1–190 of the E3L gene product at the E3L locus of the WR strain of vaccinia virus and is designated WRΔ54N.

In another preferred embodiment, the region of the viral genome encoding the N-terminal portion of the E3L gene product at the E3L locus of the WR strain of vaccinia virus contains two point mutations such that the amino acid at position 44 is changed from asparagine to alanine, and the amino acid at position 66 is changed from tryptophan to leucine, and is designated WR N44A W66L.

The present invention further provides recombinant vaccinia viral vectors comprising the recombinant vaccinia virus described above and further containing exogenous, i.e., nonvaccinia virus, DNA. Exogenous DNA may encode any desired product, including for example, an antigen, an anticancer agent, or a marker or reporter gene product. The recombinant vaccinia virus may further have deletions or inactivations of nonessential virus-encoded gene functions. Nonessential gene functions are those which are not required for viral replication in a host cell. The exogenous DNA is preferably operably linked to regulatory elements that control expression thereof. The regulatory elements are preferably derived from vaccinia virus.

The recombinant vaccinia virus of the present invention may be constructed by methods known in the art, for example by homologous recombination or site directed mutagenesis. Standard homologous recombination techniques utilize transfection with DNA fragments or plasmids containing sequences homologous to viral DNA, and infection with wild-type or recombinant vaccinia virus, to achieve recombination in infected cells. Conventional marker rescue techniques may be used to identify recombinant vaccinia virus. Representative methods for production of recombinant vaccinia virus by homologous recombination are disclosed by Piccini et al. (1987) *Methods in Enzymology* 153:545, the disclosure of which is incorporated herein by reference. Representative methods for site-directed mutagenesis are disclosed by Sarkar (1990) Biotechniques 8:404, the disclosure of which is incorporated herein by reference.

For example, the recombinant vaccinia virus of a preferred embodiment of the present invention may be constructed by infecting host cells with vaccinia virus from which the E3L gene has been deleted, and transfecting the host cells with a plasmid containing a nucleic acid encoding amino acids 84–190 or 55–190 of the E3L gene product flanked by sequences homologous to the left and right arms that flank the vaccinia virus E3L gene. The vaccinia virus used for preparing the recombinant vaccinia virus of the invention may be a naturally occurring or engineered strain. Strains useful as human and veterinary vaccines are particularly preferred and are well-known and commercially available. Such strains include Wyeth, Lister, WR, and engineered deletion mutants of Copenhagen such as those disclosed in U.S. Pat. No. 5,762,938, which is incorporated herein by reference. Recombination plasmids may be made by standard methods known in the art. The nucleic acid sequences of the vaccinia virus E3L gene and the left and right flanking arms are well-known in the art, and may be found for example, in Earl et al. (1993) in *Genetic Maps: locus maps of complex genomes*, O'Brien, ed., Cold Spring Harbor Laboratory Press, 1.157 the disclosure of which is incorporated by reference, and Goebel et al. (1990), supra. The amino acid numbering used herein is adopted from Goebel et al. (1990), supra. The vaccinia virus used for recombination may contain other deletions, inactivations, or exogenous DNA as described hereinabove.

Following infection and transfection, recombinants can be identified by selection for the presence or absence of markers on the vaccinia virus and plasmid. Recombinant vaccinia virus may be extracted from the host cells by standard methods, for example by rounds of freezing and thawing.

The resulting recombinant vaccinia virus may be further modified by homologous recombination or site directed mutagenesis to provide other deletions, inactivations, or to insert exogenous DNA.

It has been discovered in accordance with the present invention that recombinant vaccinia viruses having a mutation in the DNA encoding a N-terminal portion of the E3L gene product, and preferably a deletion of amino acids 1–83 or 1–54 of the E3L gene product, or a point mutations resulting in alanines at positions 44 and 66, maintain viral replication, protein synthesis and interferon-resistance that is indistinguishable from wild-type virus, but have remarkably reduced pathogenicity in mice relative to wild-type vaccinia virus of the same strain. Further, immunization of mice with the recombinant viruses of the present invention protects mice from infection with wild type virus.

The present invention further provides a composition comprising the recombinant vaccinia virus of the invention and a carrier. Also provided is a composition comprising the recombinant vaccinia viral expression vector of the invention and a carrier. The term carrier as used herein includes any and all solvents, diluents, dispersion media, antibacterial and antifungal agents, microcapsules, liposomes, cationic lipid carriers, isotonic and absorption delaying agents, and the like.

The recombinant vaccinia viruses and compositions of the present invention may be used as expression vectors in vitro for the production of recombinant gene products, or as delivery systems for gene products, as human or veterinary vaccines, or anticancer agents. Such utilities for recombinant vaccinia viruses are known in the art, and disclosed for example by Moss (1996) "Poxviridae: The Viruses and Their Replication" in *Virology*, Fields et al., eds., Lippincott-Raven, Philadelphia, pp. 2637–2671, incorporated herein by reference.

The present invention further provides a method of making a recombinant gene product comprising subjecting a recombinant vaccinia viral vector comprising a vaccinia virus having a mutation in the region encoding amino acids 1–117 of the E3L gene product and further comprising exogenous DNA that encodes the recombinant gene product operably linked to regulatory elements that control expression thereof, to conditions whereby said recombinant gene product is expressed, and optionally recovering the recombinant gene product. In a preferred embodiment, the recombinant gene product is an antigen that induces an antigenic and/or immunogenic response when the gene product or a vector that expresses it is administered to a mammal.

All references cited herein are incorporated in their entirety.

The following nonlimiting examples serve to further illustrate the invention.

EXAMPLE 1

Construction of Recombinant Vaccinia Virus

The plasmid pMPE3ΔGPT (described by Kibler et al. (1997) *J. Virol.* 71:1992, incorporated herein by reference) was used for recombining a truncated E3L gene into the E3L locus of the WR strain of vaccinia virus. The recombination plasmid pMPE3ΔGPT is a derivative of pBSIISK (Stratagene, La Jolla, Calif.) that has had the β-galactosidase sequences deleted, and that contains sequences homologous to the left and right arms flanking the vaccinia virus E3L gene, but that lacks the E3L gene itself. The recombination plasmid contains the *E. coli* gpt gene outside the E3L flanking arms and thus allows for selection of transfected cells by treatment with mycophenolic acid (MPA).

The Aat II (blunt-ended) Sal I fragment of E3L was subcloned into the pGEM3-5T vector (described by Chang et al. (1993) *Virology* 194: 537, the disclosure of which is incorporated by reference) and subsequently cloned into the pMPE3ΔGPT recombination plasmid using Bam HI and Hind III restriction sites. The E3L fragment encodes amino acids 84–190 of the E3L gene product as numbered by Goebel et al (1990), supra, and has a deletion of the DNA encoding the N-terminal amino acids 1–83. The plasmid resulting from the cloning of the E3L fragment into pMPE3ΔGPT is designated pMP-Δ83N.

Plasmid containing Δ54N was constructed by whole-plasmid PCR using pMPE-3L as a template and constructing primers designed to make the appropriate deletion. Briefly, divergent primers were designed flanking the region to be deleted. The primers were phosphorylated on their 5' ends using T4 polynucleotide kinase (Gibco, BRL) as follows. Separate reactions were performed for each primer, containing 3 µl of primer at 50 pmol/µl, 2 units of kinase, and 1× kinase buffer (Gibco, BRL), in a final volume of 5µl and was placed at 37° C. for 25 min. 1.5 µl of each of the phosphorylated primers (50–100 pmol per reaction) were added to the following PCR reaction: 10 ng template DNA, 5 µl of 2.5 mM dNTPs (Promega), 5 µl of 10× Pfu buffer (Stratagene), and 1 unit Pfu polymerase (Stratagene). Sterile glass distilled water was added to reach a final volume of 50 µl. Controls were run without primers or polymerase to easily determine background levels of template DNA. The thermal cycle was programmed as follows: 94° C. for 4 min, then 16 cycles of (94° C. for 1 min, 50° C. for 1 min, 72° C. for 12 min). pMPE3LN44A/W66L (pMPE3L-N/W) was provided by Alan Herbert of the Massachusetts Institute of Technology.

In vivo recombination was performed in baby hamster kidney (BHK) cells. Subconfluent BHK cells were simultaneously infected with the WR strain of vaccinia virus deleted of the E3L gene (WRΔE3L) at a multiplicity of infection (MOI) of 5 and transfected with 1 g of pMP-Δ83N, pMP-Δ54N or pMP-N44A/W66L using Lipofectace (Gibco BRL). WRΔE3L was prepared by replacing the E3L gene from the WR strain of vaccinia virus with the lacZ gene, by homologous recombination with pMPE3ΔGPT in which the lacZ gene was inserted between the E3L flanking arms.

Thirty hours post infection, the cells were harvested and recombinant virus was subjected to selection as follows. Virus was extracted from infected/transfected cells by three rounds of freezing and thawing and used to infect confluent BHK cells that had been pretreated for six hours with MPA selection medium (Modified Eagle Medium (MEM) containing 10% fetal bovine serum (FBS), 10 g/ml mycophenolic acid, 250 g/ml xanthine, 15 g/ml hypoxanthine). Following infection, cells were overlayed with MPA selection medium. At 24–72 hours post infection, plaques were visible and dishes were overlayed with MPA selection medium containing 0.5% molten agarose and 0.4 g/ml X-gal (5-bromo-4-chloro-3-indolyl-β-galactoside). Blue plaques were isolated four to six hours after X-gal overlay. Two more rounds of MPA selection were performed on the isolated blue plaques.

Resolution of the in vivo recombination occurs when the MPA selection medium is removed, resulting in either recovery of the original virus, WRΔE3L (containing lacZ in the E3L locus) or a recombinant virus containing the Δ83N or Δ54N deletion of E3L or N44A/W66L in the E3L locus. MPA-resistant blue plaques were used to infect untreated rabbit kidney RK13 cells. At 24–48 hours post infection, dishes were overlayed with MEM medium containing 0.5% molten agarose and 0.4 g/ml X-gal. Both blue and clear plaques were visible. Blue plaques indicate resolution of WRΔE3L with lacZ in the E3L locus. Clear plaques indicate resolution of virus containing the Δ83N deletion of E3L in the E3L locus.

Two more rounds of infections with clear plaques were performed to purify plaques containing the desired mutation. Recombinant virus was amplified in RK13 cells.

Nucleic acid sequencing was used to confirm that the Δ83N fragment of E3L of plasmid pMP-Δ83N, the Δ54N fragment of E3L of plasmid pMPΔ54N or the N44A/W66L mutation of E3L of plasmid pMP-N44A/W66L was present in the recombinant virus. Viral DNA was extracted from cells infected by each virus. Infected cells were freeze-thawed three times, followed by a thirty second sonication. Cell debris was removed by centrifugation at 700×g for ten minutes. Nucleic acid was obtained by phenol/chloroform extraction of the supernatant, and PCR was performed using primers to the E3L flanking arms. The PCR reaction products were subjected to agarose gel electrophoresis. DNA was extracted from the band of interest and DNA sequencing was performed. The identity of the insert was determined by sequence comparison to the plasmid DNA sequence of pMP-Δ83N, pMP-Δ54N or pMP-N44A/W66L.

EXAMPLE 2

Host Range and Interferon Resistance of WR, WRΔ83N and WRΔ3L

Wild-type vaccinia virus of the WR strain (WR) and variants WRΔE3L and WRΔ83N as described in Example 1 were assessed for interferon resistance as follows.

RK13 cells were set down in six well tissue culture dishes at 70–80% confluency. Cells were treated with varying concentrations of rabbit interferon alpha (0–1000 U/ml) for sixteen hours prior to infection. Cells were infected with approximately 100 plaque forming units (pfu) of WR, WRΔE3L or WRΔ83N virus. Dishes were stained with crystal violet 24 hours post infection and plaques were counted.

WRΔE3L exhibited interferon sensitivity (as measured by plaque reduction) at a concentration of 10 Units/ml of interferon, whereas WRΔ83N and WR did not exhibit interferon sensitivity at 10 or 100 Units/ml, but both showed plaque reduction at a concentration of 1000 Units/ml.

The foregoing results indicate that WRΔE3L is sensitive to the effects of interferon, and that WRΔ83N, like WR, exhibits an interferon-resistant phenotype.

WR, WRΔE3L and WRΔ83N were assayed for host range as follows. Six-well tissue culture dishes containing RK13 cells or HeLa cells were set down simultaneously at 70–80% confluency. Both cell types were infected with equal dilutions of virus, and 24–48 hours post infection cells were stained with crystal violet and plaques were counted for each cell type. A comparison was made by determining the efficiency of plaquing (number of plaques in HeLa cells divided by number of plaques in RK13 cells) for each virus. The efficiencies of plaquing were: WR: 0.98; WRΔ83N: 1.06; WRΔE3L: <0.01.

These results indicated that WRΔE3L has a restricted host range in that it cannot replicate in HeLa cells but exhibits nearly wild-type replication in RK13 cells. WRΔ83N, like wild-type WR, replicates in RK13 cells and HeLa cells.

The foregoing results showthat WR and WRΔ83N are identical with respect to host range and interferon resistance in the cultured cells evaluated, whereas WRΔE3L is sensitive to interferon and has a restricted host range.

EXAMPLE 3

Virulence of WR, WRΔE3L and WRΔ83N

Virus (WR, WRΔE3L or WRΔ83N) was amplified by infection of RK13 cells until 100% CPE (cytopathic effect) was observed. Cells were scraped and resuspended in 1 mM Tris, pH 8.8. Amplified virus was freeze-thawed three times to release virus from cells. Debris was removed by centrifugation at 700×g for 10 min. Supernatant was used for mouse infections. Various dilutions of virus in 1 mM Tris, pH 8.8 were used in the experiment to determine LD50.

Three to four week old c57b16 mice were anesthetized by intrafemoral injection of a cocktail of ketamine, acepromazine, and xylazine. Mice were subsequently infected with 10 l of virus or a dilution of virus intranasally using a pipetman and gel loading tip. Mice were then replaced in their cages and observed daily for pathogenesis and death.

Intranasal inoculation with WR resulted in death at $10^4$ pfu, whereas no pathogenesis could be detected with WRΔE3L at the highest dose. For inoculation with WRΔ83N, $10^7$ pfu was required for death, indicating that the amino-terminus of E3L is an important determinant for virus virulence.

EXAMPLE 4

Vaccination with WR Δ83N, WR Δ54N and WR N44A W66L

Groups of five C54b16 mice were immunized with different doses (ranging from 15 to 15,000 plaque forming units) of recombinant vaccinia virus deleted of the 83 N terminal amino acids in the E3L gene (WR Δ83N). One month later the immunized mice and the unimmunized controls (mock+wt WR) were challenged with a million pfu of wt WR. Weight loss was used as an indicator of disease due to wt WR. As shown in FIG. 1, severe weight loss was observed in the unimmunized control while all the immunized mice recorded normal weight gain following challenge. 15000 pfu of the recombinant virus was sufficient to protect mice against infection with wt WR.

Figure 2:
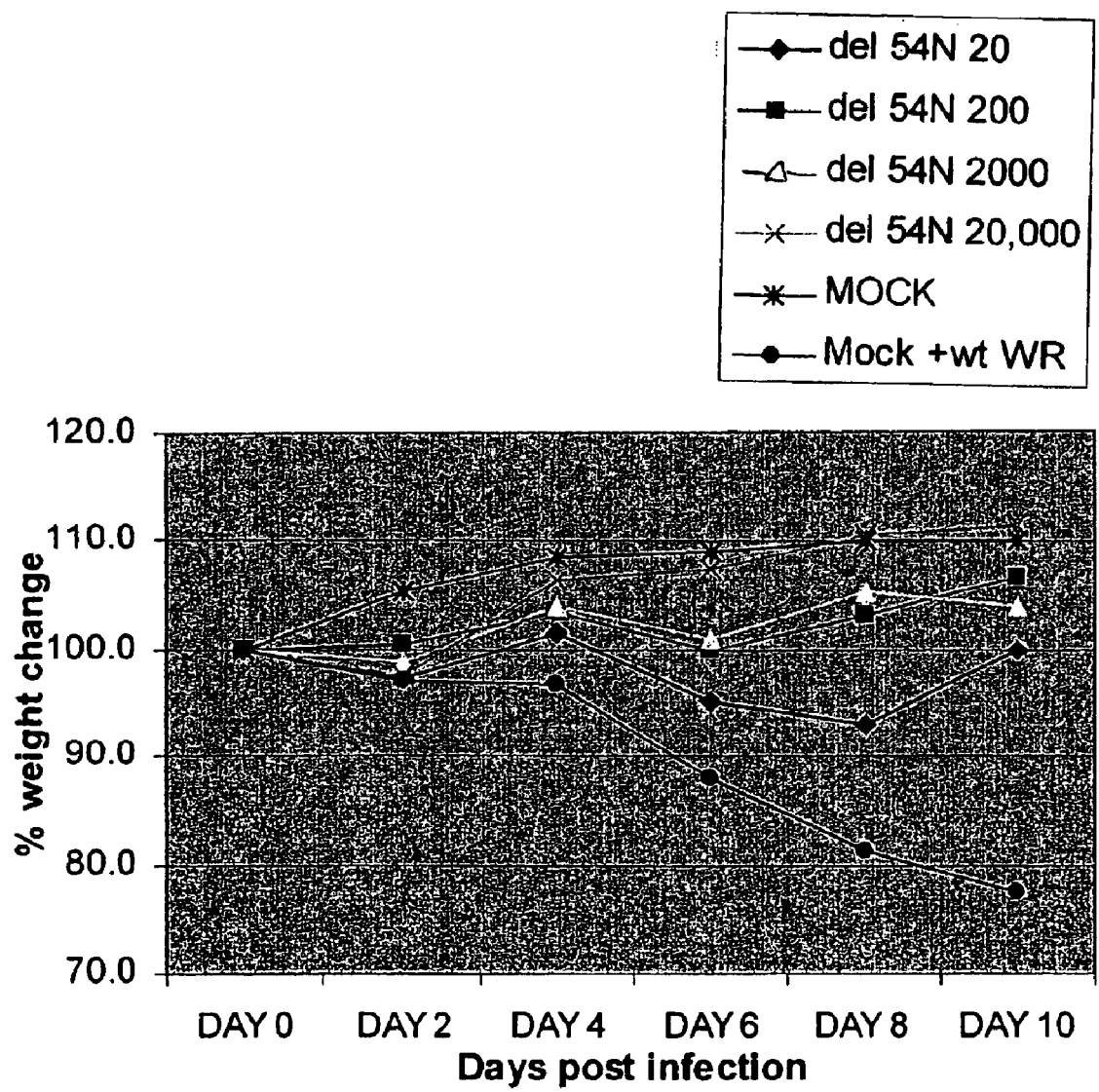
FIG. 2 is a graph showing percent weight change in mice infected with vaccinia virus following immunization with WR Δ54N.

Groups of five C57b16 mice were immunized with different doses (ranging from 20 to 20,000 plaque forming units) of recombinant vaccinia virus deleted of the 54 N terminal amino acids in the E3L gene (WR Δ54N). One month later the immunized mice and the unimmunized controls (mock+wt WR) were challenged with a million pfu of wt WR. Weight loss was used as an indicator of disease due to wt WR. As shown in FIG. 2, severe weight loss was observed in the unimmunized control while all the immunized mice recorded normal weight gain following challenge. 20000 pfu of the recombinant virus was sufficient to protect mice against infection with wt WR.

Figure 3:
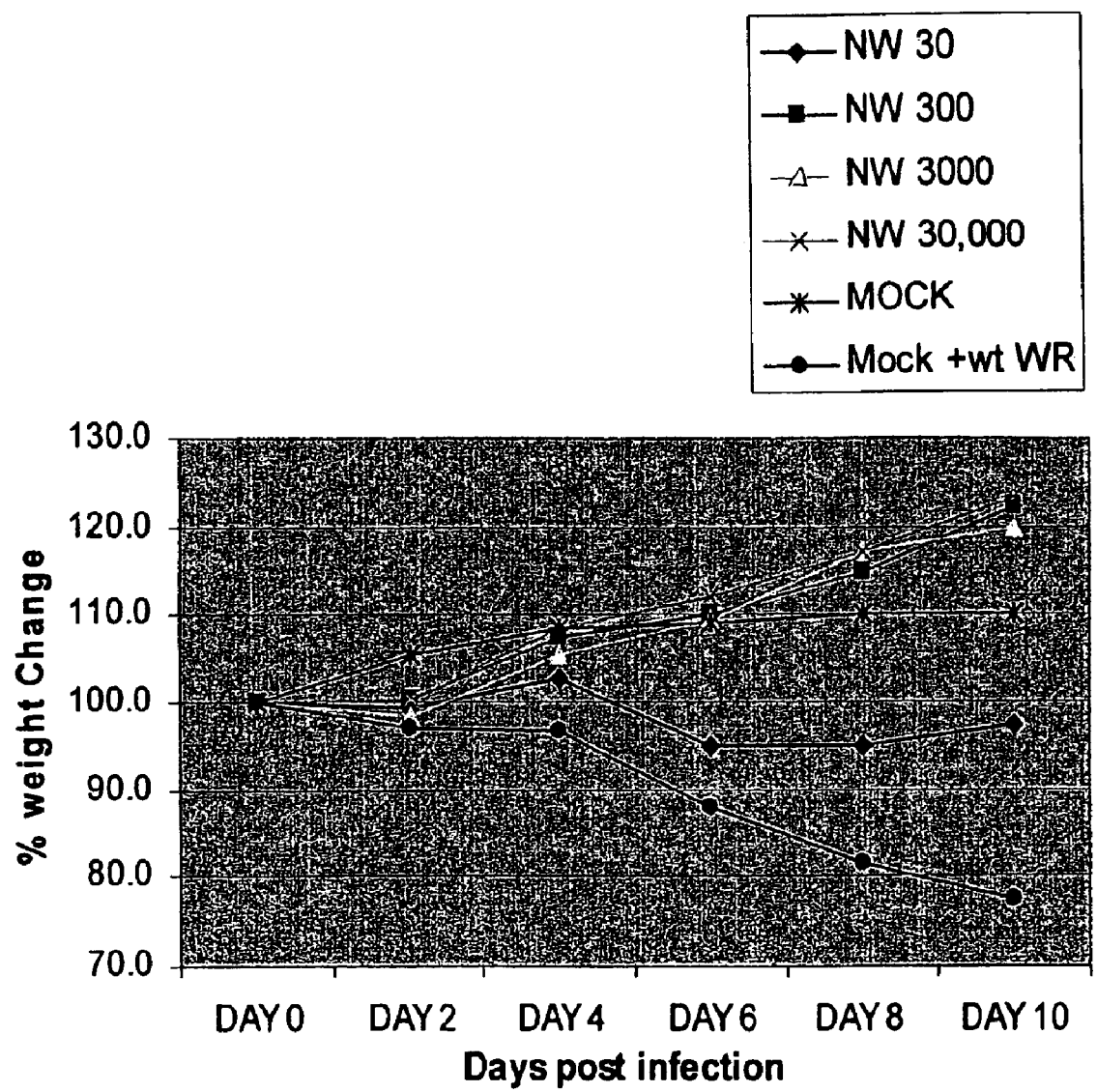
FIG. 3 is a graph showing percent weight change in mice infected with vaccina virus following immunization with WR N44A W66L.

Groups of five C57b16 mice were immunized with different doses (ranging from 30 to 30,000 plaque forming units) of recombinant vaccinia virus with 2 point mutations in the N terminus in the E3L gene (WR N44A W66L). One month later the immunized mice and the unimmunized controls (mock+wt WR) were challenged with a million pfu of wt WR. Weight loss was used as an indicator of disease due to wt WR. As shown in FIG. 3, severe weight loss was observed in the unimmunized control while all the immunized mice recorded normal weight gain following challenge. 300 pfu of the recombinant virus was sufficient to protect mice against infection with wt WR.

We claim:

1. An expression vector comprising:
   a recombinant vaccinia virus having an E3L gene
      (a) having a deletion of the region encoding amino acids 1–54 of the E3L gene product and
      (b) encoding a protein that binds dsRNA; and
   exogenous DNA and regulatory elements operably linked thereto.

2. A composition comprising the vector of claim 1 and a carrier.

3. A method of making a recombinant gene product comprising:
   subjecting an expression vector comprising:
      a recombinant vaccinia virus having an E3L gene
         (a) having a deletion of the region encoding amino acids 1–54 of the E3L gene product and
         (b) encoding a protein that binds dsRNA; and
      exogenous DNA that encodes said recombinant gene product regulatory elements operably linked thereto,
   to conditions whereby said recombinant gene product is expressed.

4. The method of claim 3 further comprising recovering said recombinant gene product.

5. The method of claim 3 wherein said recombinant gene product is an antigen.

* * * * *